United States Patent
Stevens et al.

(10) Patent No.: US 6,969,398 B2
(45) Date of Patent: Nov. 29, 2005

(54) METHOD AND APPARATUS FOR CLOSING A SEVERED STERNUM

(76) Inventors: Leonard Stevens, 3405 S. New Haven, Tulsa, OK (US) 74135; Archibald S. Miller, III, 6585 S. Yale, Suite 314, Tulsa, OK (US) 74136

( * ) Notice: Subject to any disclaimer, the term of this patent is extended or adjusted under 35 U.S.C. 154(b) by 0 days.

(21) Appl. No.: 10/699,208

(22) Filed: Oct. 31, 2003
(Under 37 CFR 1.47)

(65) Prior Publication Data
US 2004/0133206 A1 Jul. 8, 2004

Related U.S. Application Data

(63) Continuation of application No. 10/095,324, filed on Mar. 7, 2002, now abandoned, which is a continuation-in-part of application No. 10/001,988, filed on Oct. 31, 2001, now Pat. No. 6,540,769.

(51) Int. Cl.[7] .............................................. A61B 17/08
(52) U.S. Cl. ....................... 606/216; 606/213; 606/215; 606/217; 606/218; 24/526; 24/527; 24/528
(58) Field of Search .............................. 606/72, 71, 74, 606/151, 218, 216, 217, 221, 60, 213, 69, 606/157, 215; 269/89, 152; 403/388, 396; 24/526, 527, 528

(56) References Cited

U.S. PATENT DOCUMENTS

| | | | | |
|---|---|---|---|---|
| 268,632 | A | * | 12/1882 | Danforth ..................... 606/218 |
| 408,080 | A | | 7/1889 | Carroll |
| 573,685 | A | * | 12/1896 | Munro .......................... 24/528 |
| 3,147,754 | A | * | 9/1964 | Koessler ...................... 128/885 |
| 3,385,299 | A | * | 5/1968 | Le Roy ....................... 606/218 |
| 3,473,528 | A | | 10/1969 | Mishkin et al. |
| 4,201,215 | A | | 5/1980 | Crossett et al. |
| 4,279,248 | A | | 7/1981 | Gabbay |
| 4,379,358 | A | | 4/1983 | Wibrow |
| 4,512,346 | A | | 4/1985 | Lemole |
| 4,896,668 | A | | 1/1990 | Popoff et al. |
| 5,139,498 | A | | 8/1992 | Astudillo Ley |
| 5,318,566 | A | | 6/1994 | Miller |
| 5,330,489 | A | | 7/1994 | Green et al. |
| 5,356,412 | A | | 10/1994 | Golds et al. |
| 5,435,044 | A | | 7/1995 | Ida |
| 5,454,140 | A | | 10/1995 | Murai |
| 5,571,105 | A | | 11/1996 | Gundolf |
| 5,766,218 | A | | 6/1998 | Arnott |
| 5,810,825 | A | | 9/1998 | Huebner |
| 5,810,854 | A | | 9/1998 | Beach |

(Continued)

*Primary Examiner*—Glenn K. Dawson
*Assistant Examiner*—Michael Mendoza
(74) *Attorney, Agent, or Firm*—Jenkens & Gilchrist

(57) ABSTRACT

A sternal closure device including impermanently joined sliding and receiving attachment structures which are adapted for intercostal positioning between at least two corresponding rib pairs and substantially surrounding a patient's sternum with each structure having a cross member, a plurality of integrated legs and foot members, a plurality of sternum engagement surfaces, and an end portion. The receiving structure further incorporates a resiliently tensioned catch member with angularly disposed teeth like structures positioned to receive and position a plurality of receiving structure projection members when inserted therein. The catch member further serves as a stabilizing structure with stabilization facilitated via an easily removed single screw like structure markedly facilitates quick release. The projection members further embody complimenting positioned teeth like structures providing for racheting, unidirectional entry and positioning within the receiving structure, whereupon complimentary teeth engagement surfaces on catch and receiving member projection members facilitate secure and precision positioning.

16 Claims, 5 Drawing Sheets

U.S. PATENT DOCUMENTS

| | | | |
|---|---|---|---|
| 5,928,231 A * | 7/1999 | Klein et al. ................... 606/60 |
| 5,941,881 A | 8/1999 | Barnes |
| 6,051,007 A | 4/2000 | Hogendijk et al. |
| 6,217,580 B1 | 4/2001 | Levin |

* cited by examiner

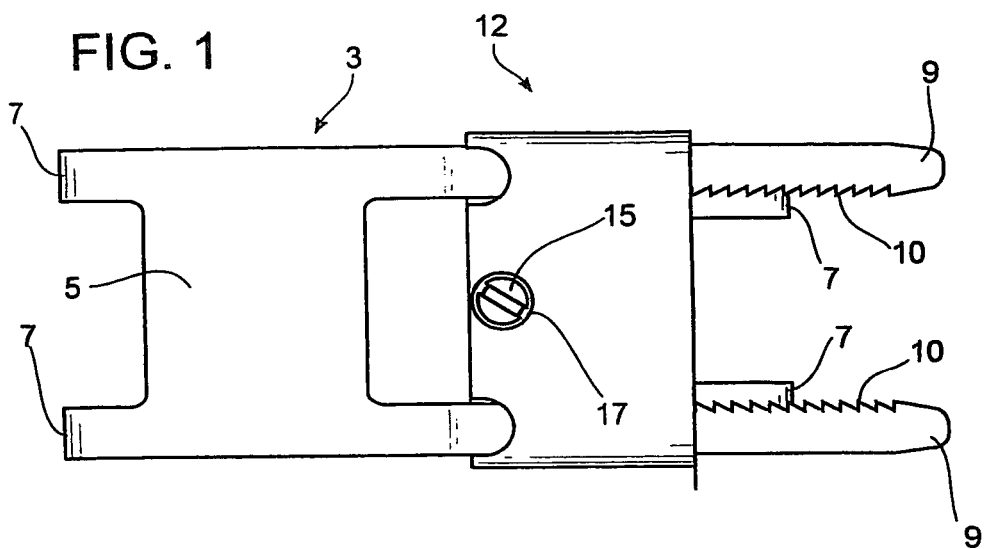
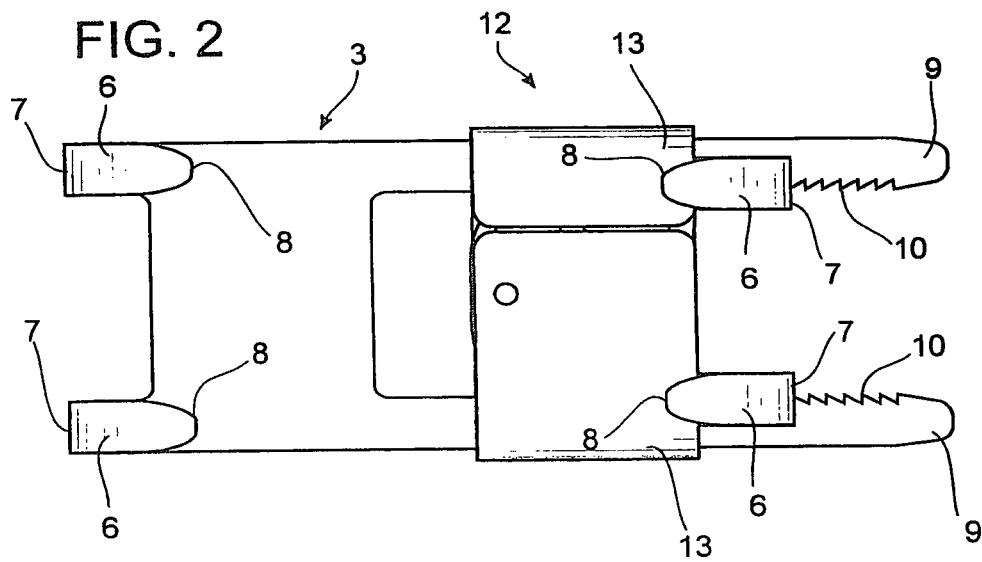

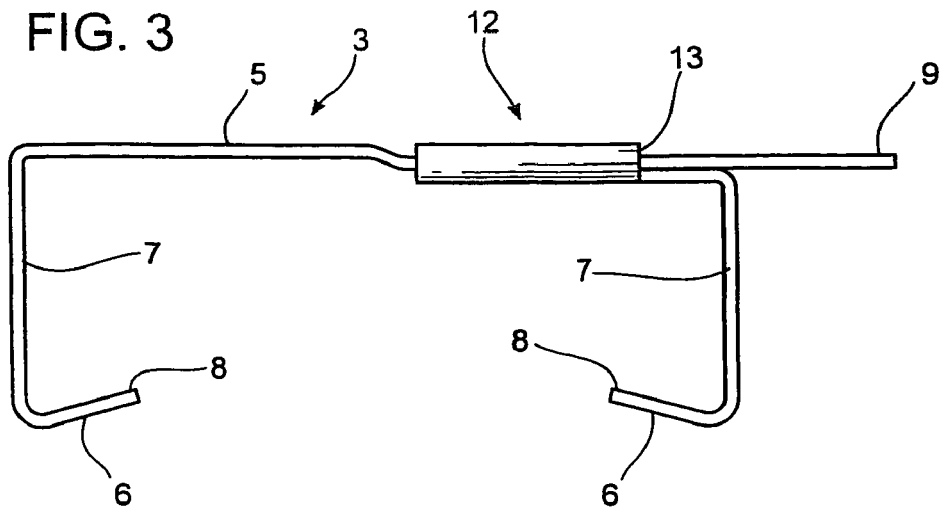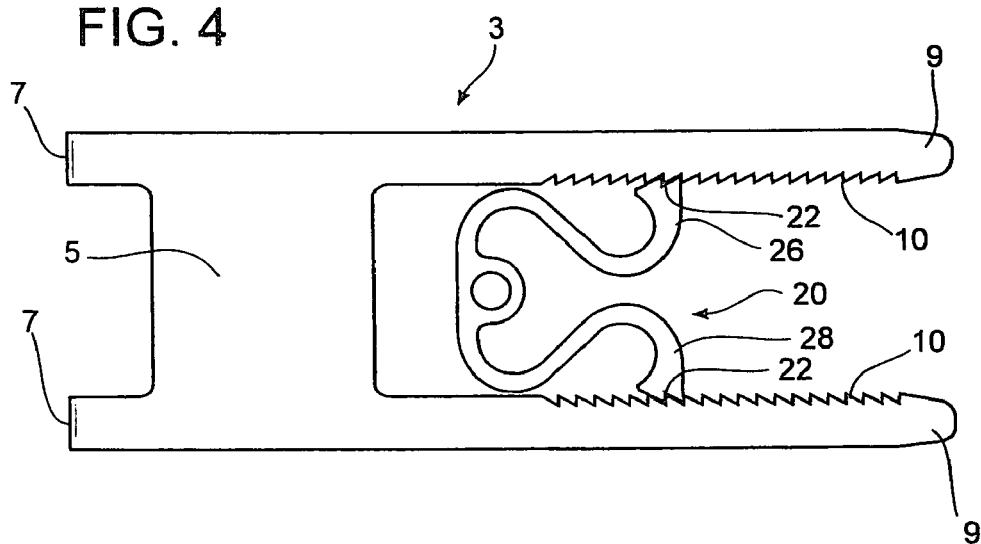

METHOD AND APPARATUS FOR CLOSING A SEVERED STERNUM

REFERENCE TO PENDING APPLICATIONS

This application is a continuation of U.S. patent application Ser. No. 10/095,324 filed Mar. 7, 2002, now abandoned which is a continuation-in-part of U.S. Ser. No. 10/001,988 filed on Oct. 31, 2001, now U.S. Pat. No. 6,540,769.

TECHNICAL FIELD OF THE INVENTION

This invention relates generally to surgical devices. More specifically, the present invention relates to improved sternum clamping devices and methods to reapproximate a patient's sternum following a partial median sternotomy.

BACKGROUND OF THE INVENTION

A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs or tissues. Following such a procedure, the two severed sternal halves must be reapproximated.

Traditionally, sternal halves have been reapproximated with stainless steel wires wrapped around or through the sternal halves so as to exert medial compression thereon and twisted together to approximate the sternum. Other methods of sternum repair include the use of band or strap assemblies which typically include a locking mechanism, which secures a strap in a closed looped configuration about the sternum positions. While utilization of steel wires and strap assemblies have been widely accepted for sternum repair, these devices present a number of disadvantages. Steel wires can and do break, and provide insufficient(non-uniform) clamping force resulting in sternal nonunion. Steel wires are difficult to maneuver and place around the sternum. The cut ends of the steel wires are also sharp and can pierce through the surgeon's gloves or fingers. In addition, the small diameter of the steel wires can cause the wires to migrate into or through the tissue surrounding the sternum region or into the sternal bone itself over time and result in sternal disintegration into small segments. This can lead to significant patient pain and discomfort in addition to slowing the postoperative recovery and increasing the risk of sternal infection. Moreover, the strap mechanisms of band assemblies are often relatively structurally complex and are difficult to precisely apply about the sternum. There are also healing problems associated with the use of steel wires and band assemblies due to improper forces exerted by these devices which can cause unwanted bone movements leading to raking and rubbing of surrounding tissue or bone.

Several other techniques of sternal reapproximation have been proposed both for primary closure following a median sternotomy and for reclosure following post-operative emergency surgical procedures. One such sternal fixation device is described in U.S. Pat. No. 6,051,007 entitled External Closure Device and Instruments Therefor, the entire contents of which are incorporated by reference.

The sternum closure device of U.S. Pat. No. 6,051,007 however is clearly absent the benefits and teachings of the instant invention. Most particularly foot portions (20, 40) of the '007 device are limited to two points of contact on the posterior section of a patient's sternum and consequently lack the stability and positioning enhancement features of the instant invention. Quite distinguishable, from the '007 patent and other devices practiced in the contemporary art is the present invention's novel structure which advances the art by allowing and encouraging divided sternal plates to be tilted upward to maximize healing surfaces in apposition to each other, thus avoiding downward plate deflection and substandard healing. Also distinguishable from devices of the contemporary art, the instant invention spans the width of at least two interspaces, thus eliminating the need for more than one device for tight/secured closure over the same sternal area. The four securing leg and foot structures of the instant invention improve pulmonary mechanics by assisting in the alignment of ribs across the sternotomy allowing for simultaneous right and left rib elevation symmetrically across the sternum and chest. The projection member structures of the instant invention leverage the tight connections provided by fascia and muscle, strengthens pulmonary compliance and allows for distribution of energy and positioning strength to be spread evenly throughout the sternum. Most distinguishable from the contemporary art, the instant invention enables fragmented segments of the sternum to be held in place for healing, as opposed to single plate structures of the contemporary art which concentrate (as opposed to distribute) energy occasionally to a crushing central point thereby allowing laterally displaced fragments to further displace.

The above is a brief description of some deficiencies in the prior art and advantages of the present invention. Other features, advantages, and embodiments of the invention will be apparent to those skilled in the art from the following description, accompanying drawings and claims.

BRIEF SUMMARY OF THE INVENTION

The present invention provides an improved device and method for re-approximating the sternal halves of a patient's sternum following a median or partial sternotomy, and facilitates ready access to the thoracic cavity during or after a medical procedure advanced the art by overcoming the sternal nonunion problems inherent in prior art devices.

The present invention advances the present art and provides for an improved sternum clamping device which employs first and second attachment structures; and angled foot members which facilitate tilting divided sternal plates upward in apposition to each other avoiding prevent downward deflection to enhance healing.

The following disclosure teaches the structure and practice of a method for a sternal closure device, which comprises impermanently joined, sliding and receiving attachment structures that are adapted for intercostal positioning between at least two correspondingly positioned rib pairs substantially surrounding a patient's sternum with each structure having a cross member, a plurality of integrated leg and foot portions, a plurality of sternum engagement surfaces, and an end portion.

Another significant object of the instant invention is to facilitate sternum closure via two separate attachment structures from opposing sides which decreases the amount of metal needed for clamping/securing structures.

An additional object of the invention is to provide for two independently adjustable locking means which distribute the strength of a sternum closure, equally and laterally, and essentially appose opposing rib segments along the same plane.

Another object of the instant invention is to provide a device wherein the width of two separate sequentially occurring rip intraspaces are associated with the invention's clamping structures to eliminate need for multiple devices to facilitate sternum closure over the same area.

A further object of the instant invention is to provide a small locking member and clamping apparatus which results in decreased apparatus profile and weight but not closure strength.

Yet another object of the instant invention is to provide for a single locking mechanism which improves pulmonary mechanics by assisting in the alignment of the ribs across a sternotomy, thus permitting simultaneous right and left rib elevation symmetrically across the sternum and chest.

A further object of the instant invention is to provide for a single locking mechanism which leverages ribs connected by fascia and muscle strengthening pulmonary compliance.

An additional object of the instant invention is to provide a mechanism and method by which the distribution of closure energy and strength are spread evenly throughout the sternum enabling even fragmented segments of the sternum to be held in place for healing.

Yet another object of the instant invention is to provide an apparatus by which the strength of the sternal closure is actually increased and distributed by means of a double clamping mechanism over a correspondingly positioned rib pair.

An additional further object of the instant invention is to provide an apparatus by which the alignment of apposing ribs actually increases the strength of the closure as well as pulmonary force expiratory volume.

Yet another object of the instant invention is to provide an apparatus in which the edges are smooth to prevent dehiscence or extrusion.

Another object of the instant invention is to provide for an easily accessible and expeditious means by which sliding and receiving attachment structures may be engaged to, and disengaged from on another.

Another object of the instant invention is its single set screw which when removed, allows rapid, complete disarticulation of the apparatus allowing almost instantaneous surgical access in the event of an emergency procedure.

Additional objects and advantages of the invention are set forth, in part, in the description which follows and, in part, will be apparent to one of ordinary skill in the art from the description and/or from the practice of the invention. These together with other objects of the invention, along with the various features of novelty which characterize the invention, are pointed out with particularity in the claims annexed to and forming a part of this disclosure. For a better understanding of the invention, its operating advantages and the specific objects attained by its uses, reference would be had to the accompanying drawings, depictions and descriptive matter in which there is illustrated preferred embodiments and results of the invention.

DESCRIPTION OF THE DRAWINGS

FIG. 1 illustrates a frontal view of one embodiment of the instant invention as practiced in its joined or associated state.

FIG. 2 illustrates a posterior view of one embodiment of the instant invention as practiced in its joined or associated state.

FIG. 3 illustrates a side view of one embodiment of the instant invention as practiced in its joined or associated state.

FIG. 4 illustrates distinguishable elements of one embodiment of the instant invention in a disassociated state.

DETAILED DESCRIPTION OF THE PREFERRED EMBODIMENT

Figure 5:
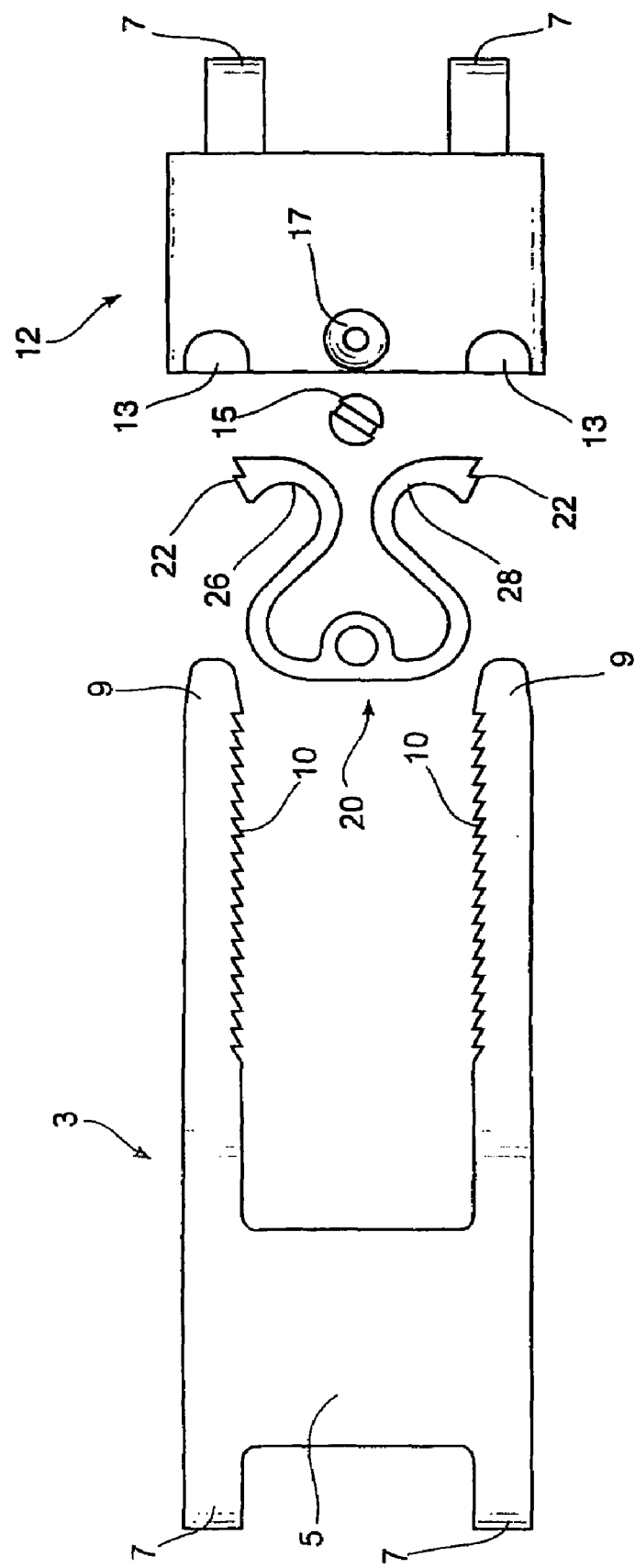
FIG. 5 illustrates a posterior view of one embodiment of the instant invention's sliding attachment structure with the invention's locking member positioned therein.

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is clear that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

Referring to the drawings like numerals indicate like elements, one embodiment of an improved sternal closure device according to the present invention is shown in FIGS. 1 through 7.

The following disclosure teaches the structure and practice of a method for a sternal closure device, which comprises impermanently jawing, sliding and receiving attachment structures that are adapted for intercostal positioning between at least two correspondingly positioned rib pairs substantially surrounding a patient's sternum with each structure having a cross member, a plurality of integrated leg and foot portions, a plurality of sternum engagement surfaces, and an end portion.

FIG. 1 illustrates a frontal view of one embodiment of the instant invention when practiced in a joined or associated state. As can be seen in FIG. 1, a sliding attachment structure 3 comprises a cross member 5, a plurality of leg structures 7, and a plurality of projection members 9 with each projection member further embodying a number of angularly disposed teeth like structures 10 which are inwardly disposed and positioned on the innermost edges of each said projection members 9.

Continuing with FIG. 1, the projection members 9 are inserted through, generally u-shaped receiving chambers formed on the lower most surface of receiving attachment structure 12 (receiving chamber not shown in FIG. 1, discussed further in association with FIG. 2). Also shown in FIG. 1, is a connection means, such as but not limited to, a screw, lock, pin, or other similarly intended device 15 and a catch member (illustrated in association with FIGS. 4 and 5) which is inserted through an aperture 17 embodied within said receiving attachment structure 12. Said connection means providing an easily accessible and expeditious means of engaging and disengaging attachment structures 3 and 12, thereby allowing rapid removal of said structure.

FIG. 2 illustrates a posterior view of one embodiment of the instant invention as practiced in its joined or associated state. Turning now to FIG. 2.

In FIG. 2, the invention's receiving attachment structure 12 is shown further illustrating its receiving chambers 13 through which the invention's projection members 9 are inserted. FIG. 2 further discloses a plurality of sternum engagement surfaces 8, which are located at the terminus of the invention's integrated leg portions 7. In practice, the invention's projection members 9 are slidably received into and through said receiving chambers 13 whereupon the invention's projection members teeth like structures 10 are correspondingly engaged by a locking member (not shown) teeth like structures, such that one way traversing of said receiving chambers 13 is allowed. The teeth like structures 10 of each projection member 9 and locking member further possess complimenting engagement surfaces which allow for secure positioning once a desired closure position has been realized. Further discussion and disclosure of the interaction between the instant invention's locking member and projection member teeth like surfaces will be provided in association with FIGS. 4 and 5.

FIG. 3 illustrates a side view of one embodiment of the instant invention as practiced in a joined or associated state. Turning now to FIG. 3.

In FIG. 3, further distinction may be observed with respect to the invention's leg 6, foot 7, and sternum engagement surfaces 8. A side view illustration of the engagement of the inventions receiving chamber 13 is also provided, as is a beveled or otherwise angled projection member positioning limitation structure 18. Said limitation structure 18 intended to provide the means by which a maximum projection member insertion may be observed/facilitated.

FIG. 4 illustrates distinguishable elements of one embodiment of the instant invention in a dis-associated state. Turning now to FIG. 4.

In FIG. 4, the invention's locking member 20 may be observed. The locking member is a resiliently tensioned structure, typically, though not limitedly embodied of the same material as the invention's receiving and sliding attachment structures 3 and 12. The catching member 20 further possess angularly disposed teeth like structures 22 which are outwardly positioned at first and second ends (26, 28) of the catching member. A securing aperture 24 is substantially centered between said ends (26, 28). FIG. 4 further provides a frontal view of the invention's sliding member as well as a posterior view of the invention's attachment receiving structure 12.

FIG. 5 illustrates a frontal view of one embodiment of the instant invention's sliding attachment structure 12 with the invention's locking member 20 positioned therein. Turning now to FIG. 5.

In FIG. 5, the invention's projection members 9 are shown for purposes of illustration and full and complete disclosure with inwardly positioned angularly disposed teeth like structures 10 located on each of the invention's projection members. Said teeth like structures 10 engaging in outwardly positioned teeth like structures 22 located at first and second ends (26, 28) of the invention's locking member 20. As the invention's locking member is housed and accommodated within the posterior of the invention's receiving chambers, FIG. 5 allows comprehension and appreciation of the one way insertion orientation of the slidably adjustable sternum closure device.

Figure 6:
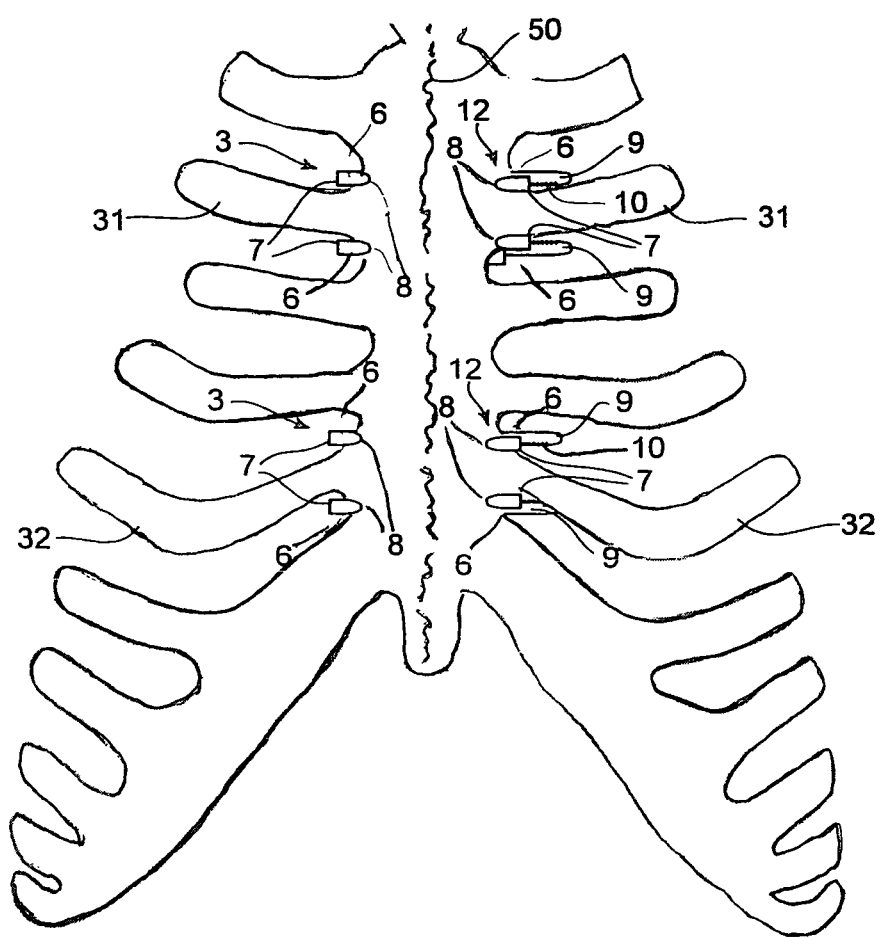
FIG. 6 illustrates a posterior view of the instant invention intercostally positioned above and below at least two correspondingly positioned rib pairs and substantially surrounding a patient's sternum.

FIG. 6 illustrates a posterior view of the instant invention intercostally positioned above and below at least two correspondingly positioned rib pairs (31, 32) and substantially surrounding a patient's sternum (50).

Figure 7:
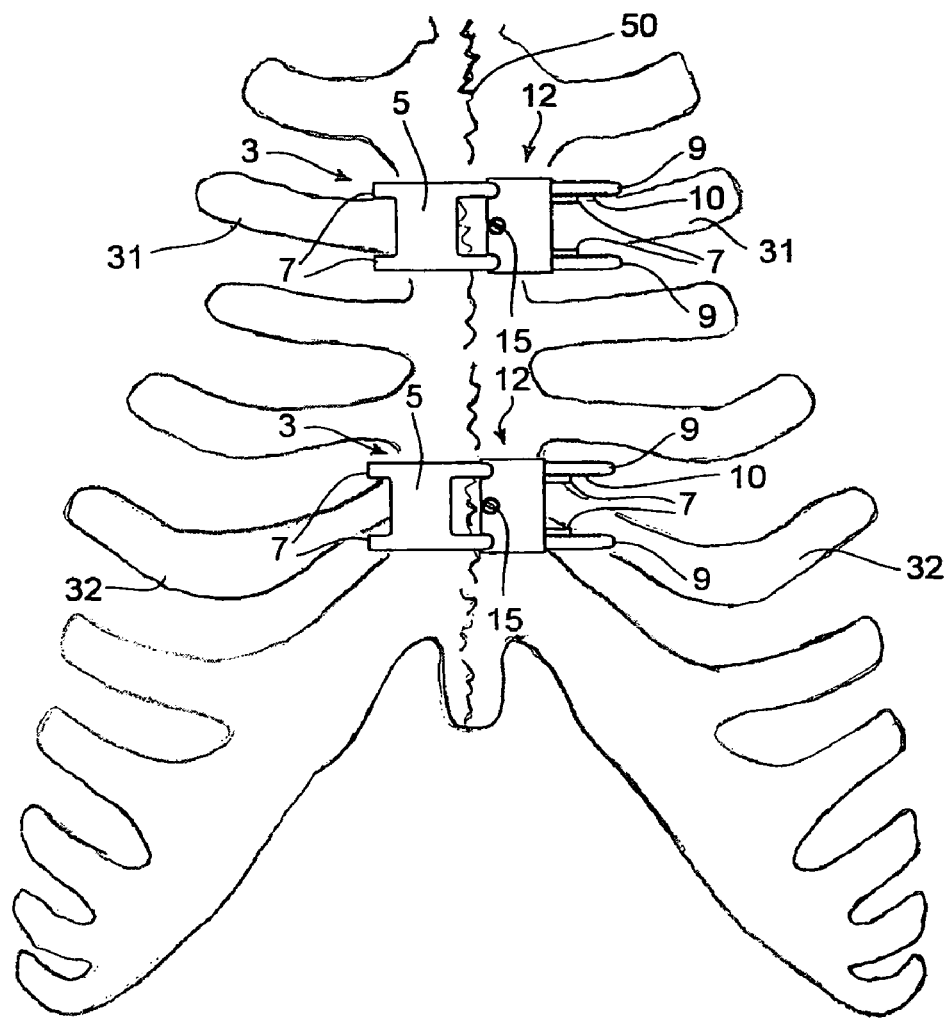
FIG. 7 illustrates a frontal view of the instant invention intercostally positioned above and below at least two correspondingly positioned rib pairs and substantially surrounding a patient's sternum.

FIG. 7 illustrates a frontal view of the instant invention intercostally positioned above and below at least two correspondingly positioned rib pairs (31, 32) and substantially surrounding a patient's sternum (50).

It will be apparent to those skilled in the art that various modifications and variations can be made in the construction, configuration, and/or operation of the present invention without departing from the scope or spirit of the invention. For example, in the embodiments mentioned above, variations in the materials used to make each element of the invention may vary without departing from the scope of the invention. Thus, it is intended that the present invention cover the modifications and variations of the invention provided they come within the scope of the appended claims and their equivalents.

While this invention has been described to illustrative embodiments, this description is not to be construed in a limiting sense. Various modifications and combinations of the illustrative embodiments as well as other embodiments will be apparent to those skilled in the art upon referencing this disclosure. It is therefore intended that this disclosure encompass any such modifications or embodiments.

What is claimed is:

1. A sternal closure device comprising impermanently joined sliding and receiving attachment structures which are adapted for intercostal positioning between at least two correspondingly positioned rib pairs substantially surrounding a patient's sternum each structure having a cross member, a plurality of integrated leg and angled foot portions, and a plurality of sternum engagement surfaces, and an end portion; and wherein the receiving attachment structure further comprises a resiliently tensioned locking member with angularly disposed teeth like structures outwardly positioned at first and second ends of said resiliently tensioned locking member and a securing aperture substantially centered there between; and wherein said resiliently tensioned locking member may be compressed to facilitate immediate device disengagement when previously secured intercostally between at least two corresponding positioned rib pairs.

2. The device of claim 1 wherein said sliding structure further comprises a plurality of projection members with angularly disposed teeth like structures inwardly positioned on each innermost surface of each projection member.

3. The device of claim 1 wherein said sternum engagement surfaces are adapted to contact the frontal portion of a sternum.

4. The device of claim 1 wherein said sternum engagement surfaces are adapted to contact the posterior portion of a sternum.

5. The device of claim 1 wherein said sternum engagement surfaces are adapted to contact the frontal and posterior of a sternum.

6. The device of claim 1 wherein the receiving attachment structure further comprises a securing means to facilitate the operative securing of said structures to one another.

7. The surgical device of claim 1 wherein said sliding and receiving attachment structures are made from biocompatible material.

8. The surgical device of claim 7 wherein said material comprises a radiolucent biocompatible material.

9. The sternal closure device of claim 1 wherein said sliding and receiving attachment structures are sized and dimensioned to engage opposite sides of a patient's severed sternum and facilitate the tilting of divided sternal plates while positioned intercostally between at least two correspondingly rib pairs.

10. The sternal closure device of claim 1 wherein said device further comprises a screw type fastening means to removably attach said sliding and receiving attachment structures.

11. A method of closing a patient's sternum following a sternotomy comprising:
   positioning sliding and receiving attachment structures about a respective sternal half and between at least two correspondingly positioned rib pairs;
   aligning opposed positioned sliding and receiving attachment structures for subsequent insertion of sliding structure projection members into receiving chambers of said receiving attachment structure;
   positioning foot members of attachment and receiving structures upon the posterior section of said sternum in a manner to angle upwardly divided sternal halves and to maximize sternal healing surface contact; and,
   removably positioning and securing teeth like structures on each end of a resiliently tensioned locking member to abut complimenting teeth located on a plurality of projection members where said projection members are within said receiving chambers; and
   wherein said resiliently tensioned locking member may be compressed to facilitate immediate device disengagement when previously secured intercostally between at least two corresponding positioned rib pairs.

12. The device of claim 1 wherein said device may be intercostally positioned absent necessity for any secondary transfixion application or structure.

13. The device of claim 6 wherein said securing means may be removed to facilitate immediate device disengagement when previously secured intercostally between at least two corresponding positioned rib pairs.

14. The device of claim 1 further comprising laser scoring of at least one portion of said device to allow severing thereof to facilitate immediate device disengagement when previously secured intercostally between at least two corresponding positioned rib pairs.

15. A sternal closure device comprising impermanently joined sliding and receiving attachment structure which are adapted for intercostal positioning between at least two correspondingly positioned rib pairs substantially surrounding a patient's sternum each structure having a cross member, a plurality of integrated leg and angled foot portions, and a plurality of sternum engagement surfaces, and an end portion, wherein said device may be intercostally positioned absent necessity for any secondary transfixion application or structure; and
   wherein said receiving attachment structure further comprises a resiliently tensioned locking member with angularly disposed teeth like structures outwardly positioned at first and second ends of said resiliently tensioned locking member and a securing aperture substantially centered there between; and
   wherein said resiliently tensioned locking member may be compressed to facilitate immediate device disengagement when previously secured intercostally between at least two corresponding positioned rib pairs.

16. A sternal closure device comprising impermanently joined sliding and receiving attachment structure which are adapted for intercostal positioning between at least two correspondingly positioned rib pairs substantially surrounding a patient's sternum each structure having a cross member, a plurality of integrated leg and angled foot portions, and a plurality of sternum engagement surfaces, and an end portion, the device further comprising a laser scoring of at least one portion of said device to allow severing thereof to facilitate immediate device disengagement when previously secured intercostally between at least two corresponding positioned rib pairs; and
   wherein the receiving attachment structure further comprises a resiliently tensioned locking member with angularly disposed teeth like structures outwardly positioned at first and second ends of said resiliently tensioned locking member and a securing aperture substantially centered there between; and
   wherein said resiliently tensioned locking member may be compressed to facilitate immediate device disengagement when previously secured intercostally between at least two corresponding positioned rib pairs.

* * * * *

UNITED STATES PATENT AND TRADEMARK OFFICE
CERTIFICATE OF CORRECTION

PATENT NO.        : 6,969,398 B2
APPLICATION NO. : 10/699208
DATED             : November 29, 2005
INVENTOR(S)       : Leonard Stevens et al.

It is certified that error appears in the above-identified patent and that said Letters Patent is hereby corrected as shown below:

Column 7, line 45,   Replace "comprising laser scoring"
Claim 14             With --comprising a laser scoring--

Column 8, line 4,    Replace "attachment structure"
Claim 15             With --attachment structures--

Column 8, line 24,   Replace "attachment structure"
Claim 24             With --attachment structures--

Signed and Sealed this

Seventeenth Day of April, 2007

JON W. DUDAS
*Director of the United States Patent and Trademark Office*